United States Patent [19]

Oyama et al.

[11] Patent Number: 5,192,417
[45] Date of Patent: * Mar. 9, 1993

[54] LITHIUM ION SENSOR

[75] Inventors: Noboru Oyama, Fuchu; Toshiyuki Shono, Suita, all of Japan

[73] Assignee: Terumo Kabushiki Kaisha, Tokyo, Japan

[*] Notice: The portion of the term of this patent subsequent to Mar. 28, 2006 has been disclaimed.

[21] Appl. No.: 593,520

[22] Filed: Oct. 5, 1990

Related U.S. Application Data

[63] Continuation of Ser. No. 246,758, Sep. 20, 1988, abandoned.

[30] Foreign Application Priority Data

Sep. 21, 1987 [JP] Japan ................... 62-234956

[51] Int. Cl.$^5$ ............................................ G01N 27/30
[52] U.S. Cl. ..................................... 204/418; 128/635; 204/153.15; 257/253
[58] Field of Search ....................... 204/153.15, 418; 357/25; 128/635

[56] References Cited

U.S. PATENT DOCUMENTS

| | | | |
|---|---|---|---|
| 3,598,713 | 8/1971 | Baum et al. | 204/418 |
| 3,926,764 | 12/1975 | Ruzicka et al. | 204/435 |
| 3,932,233 | 1/1976 | Ruzicka et al. | 204/418 |
| 3,957,612 | 5/1976 | Niedrach et al. | 204/414 |
| 3,957,613 | 5/1976 | Macur | 204/412 |
| 4,020,830 | 5/1977 | Johnson et al. | 204/418 X |
| 4,052,285 | 10/1977 | Dobson | 204/420 |
| 4,115,209 | 9/1978 | Freiser et al. | 204/1 T |
| 4,198,851 | 4/1980 | Janata | 73/23 |
| 4,214,968 | 7/1980 | Battaglia et al. | 204/416 |

(List continued on next page.)

FOREIGN PATENT DOCUMENTS

| | | |
|---|---|---|
| 56283 | 7/1982 | European Pat. Off. . |
| 0186210 | 7/1986 | European Pat. Off. . |
| 3134760A | 9/1982 | Fed. Rep. of Germany . |
| 52-30490 | 8/1977 | Japan . |
| 57-63444 | 4/1982 | Japan . |
| 60-52759 | 3/1985 | Japan . |
| 60-73351 | 4/1985 | Japan . |
| 60-73551 | 4/1985 | Japan . |
| 21055 | 1/1987 | Japan ................... 204/418 |
| 898314 | 1/1982 | U.S.S.R. . |

OTHER PUBLICATIONS

T. Matsuo et al., Sensors and Actuators, 9, 115–123, (1986).

E. Pretsch et al., Research/Development, vol. 25, No. 3, p. 20–23, Mar. 1974.

Norov et al., "Calcium-Selective Electrode Without an Internal Reference Soluting" Journal of Analytical Chemistry, vol. 34, No. 8, Part 1, Aug. 1979, pp. 1139–1162.

Oyama et al., "Hydrogen Ion Selective Microelectrode Prepared by Modifying an Electrode with Polymers", Analytical Chemistry 1987, vol. 59, pp. 258–262, Jan. 1987.

(List continued on next page.)

Primary Examiner—John Niebling
Assistant Examiner—William T. Leader
Attorney, Agent, or Firm—Burns, Doane, Swecker & Mathis

[57] ABSTRACT

A lithium ion sensor includes a FET, a redox layer having a redox function covering a gate isolating membrance of the FET, and a lithium ion-sensitive layer selectively sensing lithium ion covering the redox layer.

6 Claims, 6 Drawing Sheets

U.S. PATENT DOCUMENTS

| | | | |
|---|---|---|---|
| 4,280,889 | 7/1981 | Szonntagh | 204/435 |
| 4,282,079 | 8/1981 | Chang et al. | 204/420 |
| 4,305,802 | 12/1981 | Koshiishi | 204/418 |
| 4,361,473 | 11/1982 | Young et al. | 204/418 |
| 4,454,007 | 6/1984 | Pace | 204/1 T |
| 4,504,368 | 3/1985 | Delton et al. | 204/1 T |
| 4,512,870 | 4/1985 | Kohara et al. | 204/416 |
| 4,549,951 | 10/1985 | Knudson et al. | 204/416 |
| 4,563,263 | 1/1986 | Oyama et al. | 204/418 |
| 4,615,954 | 10/1986 | Solomon et al. | 429/27 |
| 4,632,732 | 12/1986 | Fog et al. | 204/1 T |
| 4,770,759 | 9/1988 | Young et al. | 204/418 |
| 4,798,664 | 1/1989 | Yamaguchi et al. | 204/418 |

OTHER PUBLICATIONS

Oyama, "Ion Selective Microelectrode Prepared by Modifying an Electrode with Polymers" Int. Electrical Symposium, Schaumberg, IL, May 27–29, 1987; p. 122.

Oyama et al., "A New Type of Ion-Selective Microelectrodes Using Electropolymerized Thin Films", j–4 Bioelectroanalytical Chemistry Symposium, Honolulu, Oct. 18–23, 1987.

Oyama et al., "Ion Selective Electrode Prepared by Mofifying an Electrode with Polymers", Tokyo Seminar on Macromolecular Complexes, Tokyo, Univ. Oct. 14, 1987.

Oyama et al., "Electrochemical Properites of Electropolymerized Poly(1-Pyrinamie) Films", Bull Chem Soc., Japan 59, 2071–2080 (1986).

Ryan, "Electrochemical Detectors Fundamental Aspects and Analytical Application Plenum Press", Apr. 26, 1985), p. 7.

Ma et al., "Organic Analysis Using Ion-Sensitive Electrode", Academic Press, 1982, pp. 62 & 70.

Ammann, "Ion Selective Microelectrode", Springer-Verlang, New York, pp. 5–7.

Tamura et al., "Coated Wire Sodium- and Potassium-Electrode Based on Bis(Crown Ether) Compounds", Analytical Chemistry, vol. 54, No. 7, Jun. 1982, pp. 1224–1227.

Wuthier et al., "Tin Organic Compounds as Neutral Carriers for Anion Selective Electrodes", Analytical Chemistry, vol. 56, No. 3, Mar. 1984, pp. 535–538.

Koyama et al., "New Lithium Sensor Effective in Preventing Excessive Administration of Medicine," *Nihon Kohgyo Shinbun*, Sep. 7, 1987.

Patent Abstracts of Japan, vol. 9, No. 122, May 28, 1985, Japanese Kokai No. 60-7357.

*Patent Abstracts of Japan*, vol. 9, No. 122, May 28, 1985, Japanese Kokai No. 60-7357.

*Patent Abstracts of Japan*, vol. 8, No. 159, Jul. 24, 1984, Japanese Kokai No. 59-57156 (Apr. 2, 1984).

*Patent Abstracts of Japan*, vol. 7, No. 48 (P-178), Feb. 24, 1983, Japanese Kokai No. 57-196,116.

Kimura et al., Journal of the Chemical Society Perkin Transactions II 1986 "Synthesis and Selectivity for Lithium of Lipophilic 14-Crown-4 Derivatives Bearing Bulky Substitutents or an Additional Binding Site in the Side Arm".

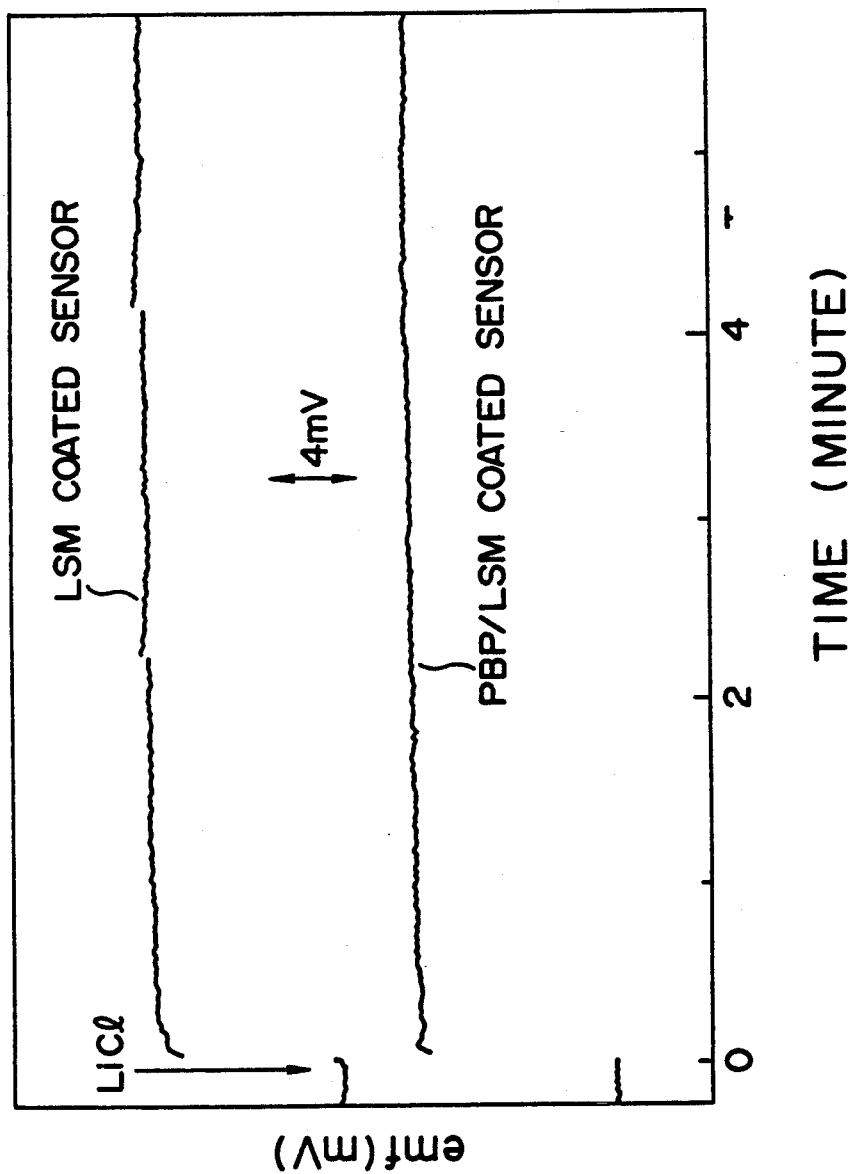
F I G. 2

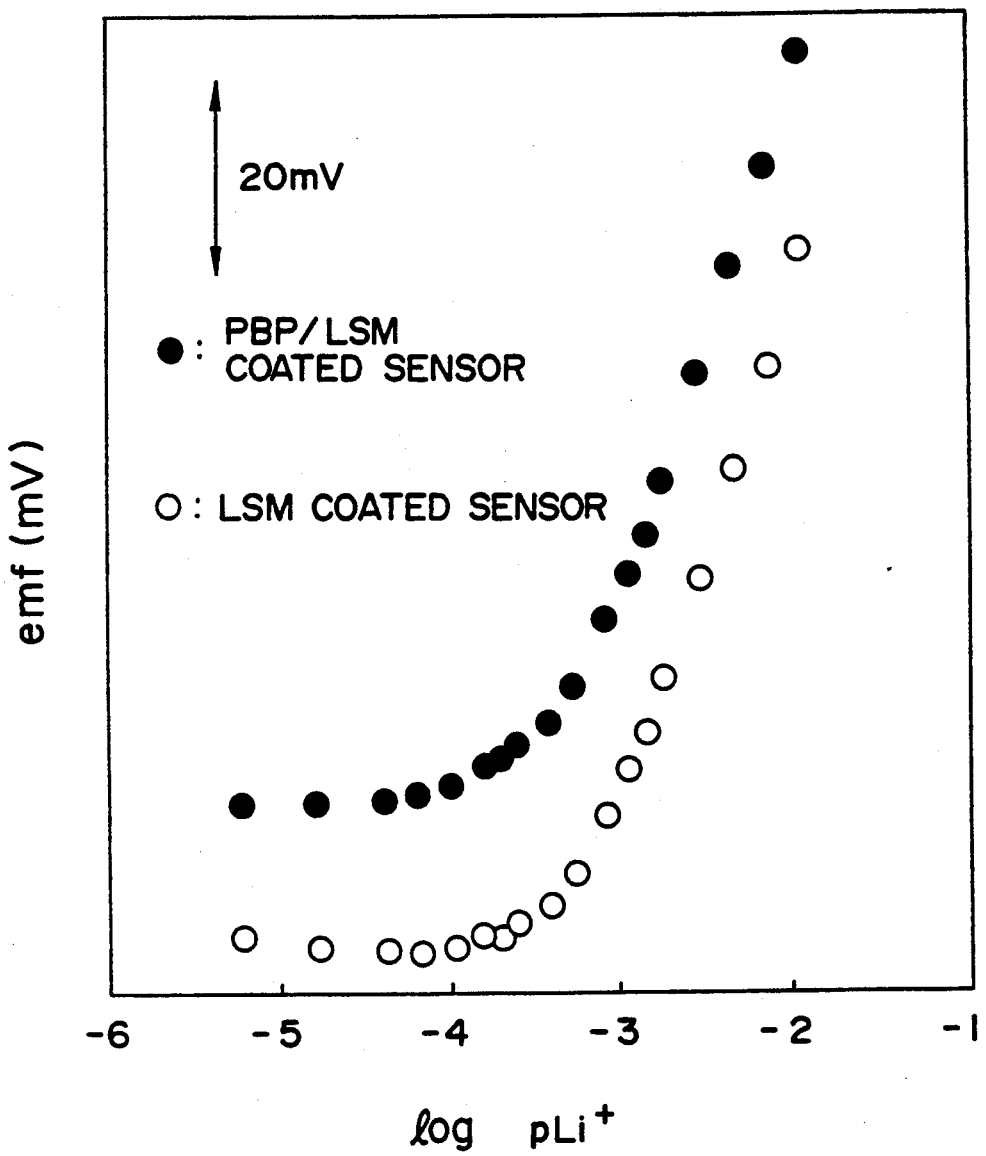
F I G. 3

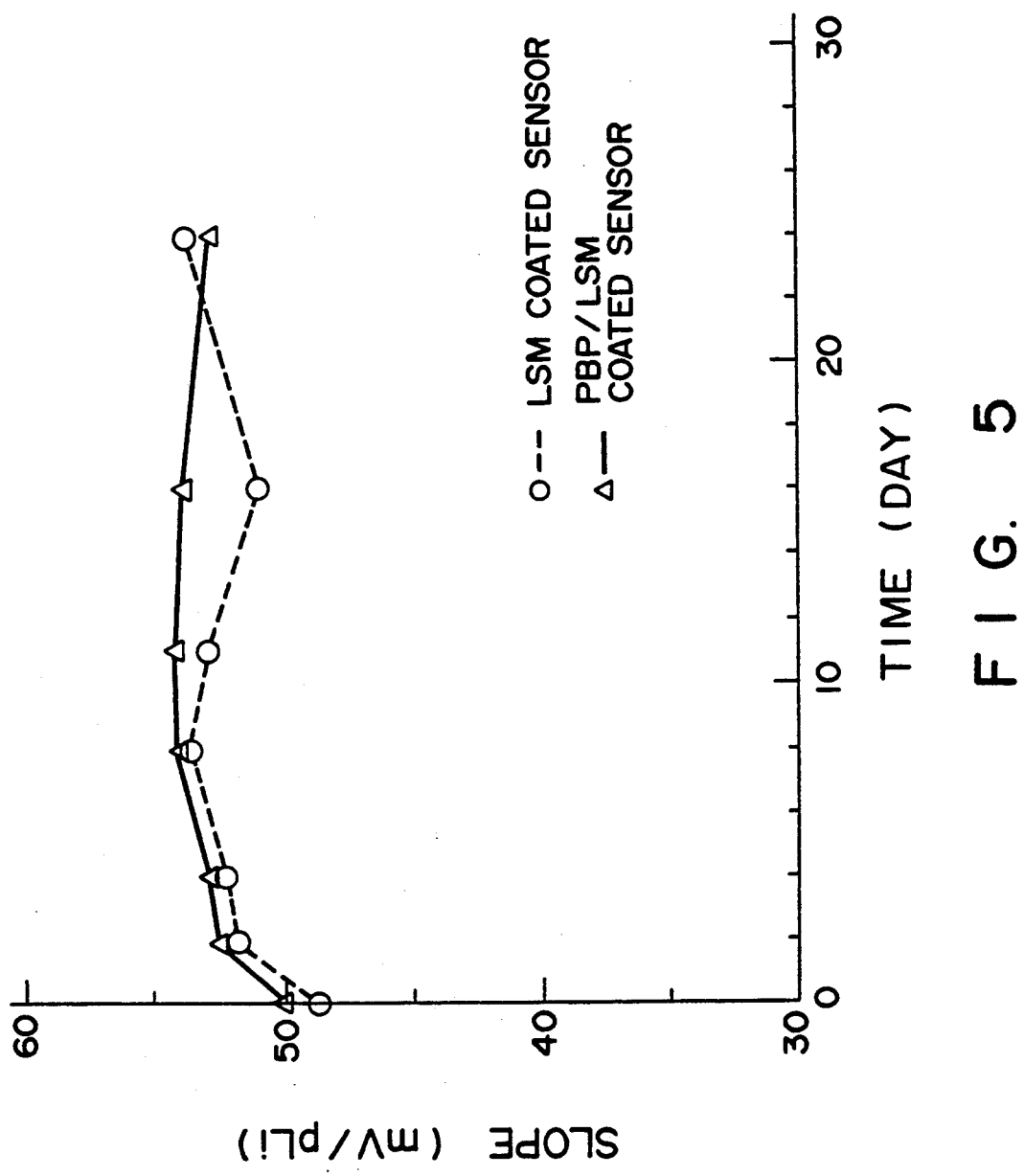

E ( V vs. SSCE )

LITHIUM ION SENSOR

This application is a continuation of application Ser. No. 246,758, filed Sep. 20, 1988, now abandoned.

BACKGROUND OF THE INVENTION

This invention relates to a lithium ion sensor and more particularly, to a lithium ion sensor for measuring a lithium ion concentration in circulatory organs in a body which changes upon administration of lithium carbonate used in a therapy for manic depressive psychosis.

In pathologic physiology of manic depressive psychosis, it is found that depression is caused by reserpine which drains intracerebral monoamine and a medicine (thymoleptics) for depression enhances an effect of monoamine. Therefore, a monoamine hypothesis assumes that depression is caused when one or both of noradrenaline and serotonin are reduced and mania is caused when they are increased. However, analysis of blood, urea, bone marrow fluids, and brain tissues of patients has not provided any definite evidence supporting this hypothesis to date. Therefore, lithium carbonate is often used to cure depression because it is assumed to suppress effects of intracerebral monoamine and serotonin.

Detection of a lithium ion concentration and its change in circulatory organs in a body caused by lithium carbonate is essential in determining the cause of manic depressive psychosis or developing a medical treatment therefor. However, a lithium ion sensor having a high response speed and good precision has not been available yet. In addition, a demand has arisen for a sensor which can be safely used for continuous measurement in circulatory organs or a body over a long time period and which has stable characteristics.

SUMMARY OF THE INVENTION

It is an object of the present invention to provide a lithium ion sensor having a high response speed and good measuring precision.

It is another object of the present invention to provide a lithium ion sensor which is safe in a body and can stably measure over a long time period.

It is still another object of the present invention to provide a lithium ion sensor which can be preserved over a long time period.

In order to achieve the above objects, a lithium ion sensor according to the present invention comprises a FET, a redox layer having a redox function covering a gate isolating membrane of the FET, and a lithium ion-sensitive layer selectively sensing lithium ion covering the redox layer.

In addition, the lithium ion sensor according to the present invention comprises an electrically conductive substrate, a redox layer having a redox function covering a surface of the electrically conductive substrate, and a lithium ion-sensitive layer selectively sensing lithium ion covering the redox layer.

According to the present invention, a lithium ion sensor having a high response speed and good measuring precision can be provided.

In addition, a lithium ion sensor which is safe in a body and can stably measure over a long time period can be provided.

Furthermore, a lithium ion sensor which can be preserved for a long time period can be provided.

More specifically, a lithium concentration in a body can be accurately detected and measured. In addition, influences of other ions such as sodium ion and potassium ion can be reduced.

The thickness of the lithium ion sensor can be reduced much thinner than a hair, and therefore the lithium ion sensor can be inserted in a living organism without pain.

The lithium ion sensor is not adversely affected by oxygen gas and therefore can be stably used over a month or more.

Since the lithium ion sensor is a solid-type sensor, it can be sterilized and easily handled.

The lithium ion-sensitive layer is a thin organic membrane which is not easily adversely affected by coagulation of blood in a living organism. Therefore, a countermeasure against coagulation of blood can be easily taken.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 2 is a graph showing a measurement result of a response speed of the lithium ion sensor of the embodiment;

FIG. 3 is a graph in which an output potential of the lithium ion sensor of the embodiment is plotted as a function of a lithium concentration;

FIG. 5 is a graph showing how the lithium ion sensor of the embodiment changes with time;

DESCRIPTION OF THE PREFERRED EMBODIMENT

Figure 1:
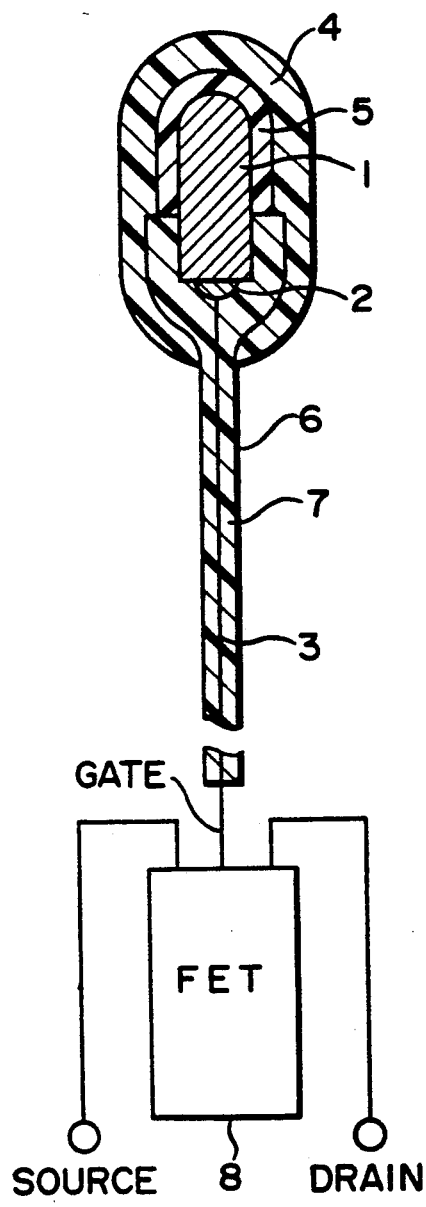
FIG. 1 is a schematic view illustrating a lithium ion sensor according to an embodiment of the present invention.

The present invention will now be described with regard to a number of examples and experiments.

An example of a FET used in the present invention is a MOSFET.

The MOSFET employed in the present invention is of the type used in ISFETs well-known in the art. If the gate isolating layer (hereafter also referred to as a gate isolating membrane where appropriate) thereof can be utilized, any MOSFET may be adopted [Matsuo and Esashi. Electrochemistry and Industrial Physics, 50, 64 (1982)]. An example which can be mentioned is one in which a FET having an $Si$-$SiO_2$ gate isolating layer is formed on a silicon or sapphire substrate. An isolated gate type MOSFET is also well-suited for use. The MOSFET using the silicon substrate is comparatively low in cost and suited for general-purpose use. The MOSFET employing the sapphire substrate is readily multiplexed is readily insulated, lends itself well to miniaturization and excels functionally.

The MOSFET can be fabricated by utilizing a conventional planar or ion injection technique. The gate isolating property can be greatly enhanced by forming an insulating film comprising $Si_3N_4$ or the like on the surface of the gate isolating layer of the MOSFET by using a CVD (chemical vapor deposition) technique or a sputtering technique.

Examples of an electrically conductive substrate used in the lithium ion sensor of the present invention are an electrically conductive carbon material such as basal plane pyrolytic graphite; hereafter referred to as BPG) and glassy carbon; and a metal such as gold, platinum, copper, silver, palladium, nickel, and iron, expecially a precious metal or a material obtained by coating the surface of any of these metals with a semiconductor such as iridium oxide or tin oxide. The electrically conductive carbon material, especially BPG is best.

In order to miniaturize the ion sensor, a stick-like electrically conductive substrate is used, and a redox layer having a redox function is deposited on its outer surface or its outer surface and 1 to 20 mm² of its distal end face. If the area is smaller than this value, a membrane resistance undesirably exceeds 50 MΩ. If the area is larger than the above value, the ion sensor cannot be miniaturized. The stick may be a column or a square pillar. However, a pillar having a round top is most preferable in terms of formability and adhesion of a membrane.

Conventionally, in BPG, a basal surface is utilized as an electrode surface. However, the present inventor has found that an edge surface of BPG can also be effectively used and therefore a stick-like electrode can be formed even by BPG. BPG is excellent especially in stability of an operation of the sensor. The diameter of a BPG stick is preferably 0.1 to 2 mm to maintain its strength if it is a column.

The electrically conductive substrate can be formed of various materials in accordance with its applications. Examples of the substrate are a substrate mainly comprising a metal/semiconductor substrate, a substrate combined with an isolated gate-type field effect transistor (FET) and coated with a carbon membrane containing a carbon material, and a substrate obtained by coating wiring of a printed circuit board with a carbon material. In addition, a composite sensor can be fabricated using a printed circuit board.

The redox layer refers to one in which a FET comprising a gate isolating membrane or electrically conductive substrate having this layer deposited on its surface is capable of generating a constant potential on the substrate owing to a redox reaction. In the present invention, an especially preferred redox layer is one which will not allow the potential to fluctuate due to the partial pressure of oxygen gas. Prticularly suitable examples of the redox layer are (1) an organic compound membrane or a polymeric membrane capable of a quinone-hydroquinone type redox reaction, (2) an organic compound membrane or polymeric membrane capable of an amine-quinoid type redox reaction, and (3) an electrically conductive substance such as poly(pyrrole) or poly(thienylene).

The quinone-hydroquinone type redox reaction is expressed by e.g. the following reaction formula, taking a polymer as an example:

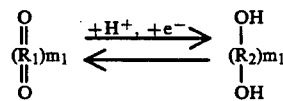

where $R_1$, $R_2$ represent e.g. compounds having a structure containing an aromatic series.

The amino-quinoid type redox reaction is expressed by e.g. the following reaction formula, taking a polymer as an example:

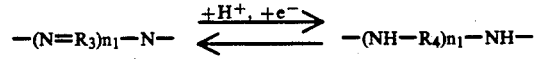

where $R_3$, $R_4$ represent e.g. compounds having a structure containing an aromatic series.

The following compounds (a)-(d) can be mentioned as compounds capable of forming the abovementioned layer having the redox function:

(a) A hydroxy aromatic compound expressed by

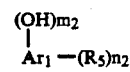

where $Ar_1$ represents an aromatic nucleus, $R_5$ a substituent group, $m_2$ is 1 or the effective valence of $Ar_1$, and $n_2$ is 0 or the effective valence of $Ar_1$ minus 1.

The aromatic nucleus of $Ar_1$ may be a single ring such as a benzene nucleus, a multiple ring such as an anthracene nucleus, pyrene nucleus, chrysene nucleus. perylene nucleus or coronene nucleus, or a heterocyclic ring. Examples of the substituent group $R_5$ are alkyl groups such as a methyl group, aryl groups such as a phenyl group, and a halogen atom.

More specifically, examples are dimethyl phenol, phenol, hydroxy pyridine, o- and m-benzyl alcohols, o-, m-, and p-hydroxybenzaldehydes, o- and m-hydroxyacetophenones, o-, m-, and p-hydroxypropiophenones, o-, m-, and p-hydroxybenzophenones, o-, m-, and p-carboxyphenols, diphenylphenol, 2-methyl-8-hydroxyquinoline, 5-hydroxy-1, 4-napthoquinone 4-(p-hydroxyphenyl)2-butanone, 1,5-dihydroxy-1,2,3,4-tetrahydronaphthalene, bisphenol-A, salicylanilide, 5- and 8-hydroquinolines, 1,8-dihydroxyanthraquinone, and 5-hydroxy-1,4-naphthoquinone.

(b) An amino aromatic compound expressed by the formula

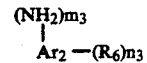

where $Ar_2$ represents an aromatic nucleus, $R_6$ a substituent group, $m_3$ is 1 or the effective valence of $Ar_2$, and $n_3$ is 0 or the effective valence of $Ar_2$ minus 1.

As for the aromatic nucleus $Ar_2$ and the substitution group $R_6$, items similar to $Ar_1$ and the substitution group $R_5$ in compound (a) can be used. Specific examples of the amino aromatic compound are aniline, 1,2-diaminobenzene, aminopyrene, diaminopyrene, aminochrysene, diaminochrysene, 1-aminophenanthrene, 9-aminophenanthrene, 9,10-diaminophenanthrene, 1-aminoanthraquinone, p-phenoxyaniline, o-phenylenediamine, p-chloroaniline, 3,5-dichloroaniline, 2,4,6-trichloroaniline, N-methylaniline, and N-phenyl-p-phenylenediamine.

(c) A quinone such as 1,6-pyrenequinone, 1,2,5,8-tetrahydroxynalizaline, phenantolinequinone, 1-aminoanthraquinone, purpurine, 1-amino-4-hydroxyanthraquinone, and anthralphyne.

Among these compounds, 2,6-xylenol and 1-aminopyrene are especially preferred.

(d) Pyrrole and derivatives thereof (e.g. N-methyl pyrrole), and thiophene and derivatives thereof (e.g. methyl thiophene).

Further, examples of compounds capable of forming the layer having the redox function are those which undergo a redox reaction. The following can be mentioned: poly(N-methyl aniline) [Onuki, Matsuda, Koyama, Nihon Kagakkaishi, 1801–1809 (1984)], poly(2,6-dimethyl-1,4-phene ether), poly(o-phenylediamine), poly(phenol) and polyxylenol; organic compounds containing the compounds (a) through (d) such as pyrazoronequinone group-containing vinyl compound-polymers, isoaroxythazine group-containing vinyl compound-polymers and other quinone group-containing compound-polymers, lower polymeric compounds (oligomers) of compounds (a) through (d), or substances obtained by fixing the compounds of (a) through (d) to polymeric compounds such as polyvinyl compounds and polyamide compounds. In the present specification, the term "polymer" is taken to mean both homopolymers and mutual polymers such as copolymers.

In the present invention, in order to deposit the compound capable of forming the redox layer on the FET gate isolating membrane or the electrically conductive substrate, a polymer obtained by synthesizing an amino aromatic compound, a hydroxy aromatic compound or the like on a FET gate isolating membrane or an electrically conductive substrate of electrically conductive carbon or a precious metal by an electrolytic oxidation polymerization method or electro-deposition method, or a polymer synthesized by application of electron beam irradiation, light or heat, is dissolved in a solvent. The resulting solution is deposited on the FET gate isolating membrane or the electrically conductive substrate by painting or dipping, reacted in the gate phase in vacuo and deposited directly on the FET gate isolating membrane or the electrically conductive substrate, or irradiated with light, heat or radiation to be deposited directly on the FET gate isolating membrane or the electrically conductive substrate. Among these three methods, the most preferred is the electrolytic oxidation polymerization method. The electrolytic oxidation polymerization method is implemented by subjecting the amino aromatic compound or hydroxy aromatic compound to electrolytic oxidation polymerization in a solvent in the presence of a suitable supporting electrolyte and depositing a layer of the polymer on the surface of the FET gate isolating membrane or the electrically conductive substrate.

Preferred examples of the solvent are acetonitrile, water, dimethyl formamide, dimethyl sulfoxide, propylene carbonate and the like.

Preferred examples of the supporting electrolyte are sodium perchlorate, sulfuric acid, sodium sulfate, phosphoric acid, boric acid, tetrafluoro-potassium phosphate, quaternary ammonium salts and the like.

The membrane thickness of the redox layer is 0.01 $\mu$m–1.0 mm, preferably 0.1 $\mu$m–0.1 mm. A membrane thickness of less than 0.01 $\mu$m does not fully bring forth the effects of the invention, while a thickness of more than 1.0 mm is undesirable from the viewpoint of miniaturizing the sensor.

The redox layer used in the present invention can be used in a form impregnated with an electrolyte. Examples of the electrolyte are phosphoric acid, dipotassium hydrogen phosphate, sodium perchlorate, sulfuric acid, tetrafluoro borate, tetraphenyl borate and the like. In order to impregnate the redox layer with the electrolyte, a simple method which can be adopted is to deposit the redox layer on the surface of the electrically conductive substrate and then dip the result into a solution of the electrolyte.

More preferably, in order to prevent transition of the lithium ion-sensitive layer to a plasticizer to improve stability of the sensor, electrolysis is started not from a monomer but from a dimer or more to cause polymerization. As a result, a dense redox layer having a high solvent resistance can be obtained.

Preferred examples of the polymer of dimer or more are those obtained by polymerizing a polymer of a hydroxy compound or an amino compound and expressed by the formulas:

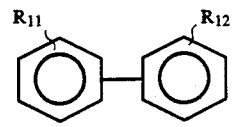

where $R_{11}$, $R_{12}$ represent OH or $NH_2$;

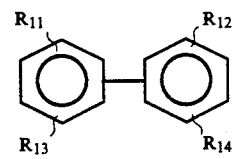

where $R_{11}$, $R_{12}$, $R_{13}$, $R_{14}$ represents OH and/or $NH_2$; and

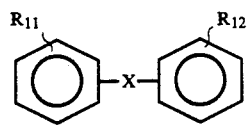

where $R_{11}$, $R_{12}$ represent OH or $NH_2$ and X represents —O—

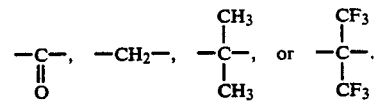

Especially, the o,o'-biphenol polymer and the p,p'biphenol polymer are preferable.

Examples of lithium ion-sensitive layer 4 are a polyvinyl chloride membrane containing dibenzyl-14-crown-4 and/or its derivative and a polyvinyl chloride layer containing dioxaheptyl-dodecyl-14-crown-4 or diethoxyphosphorioxyethyl-docecyl-14-crown-4 and/or its derivative.

In the following examples, basal plane pyrolytic graphite (hereafter referred to as BPG: manufactured by Union Carbite Co.) was used. The surface of BPG was coated with an electrolytic poly(p,p'-biphenol) polymer layer, and the surface of the electrolytic poly(p,p'-biphenol) polymer layer was coated with a polyvinyl chloride layer containing dibenzyl-14-crown-4 as a lithium ion-sensitive layer. The BPG electrode was connected to a gate terminal portion of a MOSFET, thereby fabricating a lithium ion sensor. In addition, a lithium ion sensor was fabricated by not coating the electrolytic poly(p,p'-biphenol) polymer layer but directly coating lithium ion-sensitive layer.

EXAMPLE

An example of membrane coating on an electrically conductive carbon electrode will be described below.

FIG. 1 is a schematic view illustrating a lithium ion sensor according to this example. Note that in FIG. 1, a size is not taken into consideration.

A column 1 having a diameter of 1 mm and a length of 3 mm was cut out (0.2 cm$^2$) from a plate of basal plane pyrolytic graphite (hereafter referred to as BPG: manufactured by Union Carbite Co.). A lead wire 3 (0.1-mm diameter uremet wire) was adhered on one bottom surface of the column 1 using an electrically conductive adhesive 2 (C-850-6: manufactured by Amicon Co.). Then, the column 1 was inserted in a Teflon tube 6 (inner diameter =1.3 mm) and isolated by an isolating adhesive 7 (TB2067: manufactured by Three Bond Co.), thereby fabricating a BPG electrode.

A 3-electrode cell having the above electrically conductive BPG electrode as an active electrode, a saturated sodium chloride calomel electrode (SSCE) as a reference electrode, and a platinum net as a counter electrode was used to form a redox layer and a p,p'-biphenol membrane 5 by electrolytic polymerization performed under the following electrolytic oxidation conditions.

ELECTROLYTIC OXIDATION CONDITIONS

Electrolyte:
  0.05 M p,p'-biphenol
  0.2 M sodium perchlorate
  acetonitrile (solvent)
Electrolytic temperature: 23° C.
Electrolytic conditions: After the electrolytic potential was swept 27 times from −0.2 V to +1.5 V vs. SSCE (scan rate: 50 mV/sec), electrolysis was performed for 30 min.

Figure 6A:
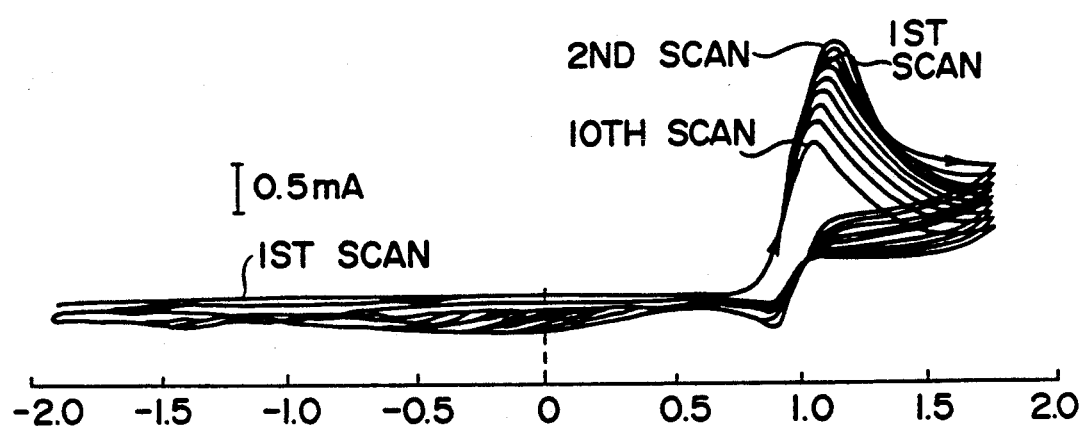
FIG. 6A is a graph showing a cyclic voltamogram.
Figure 6B:
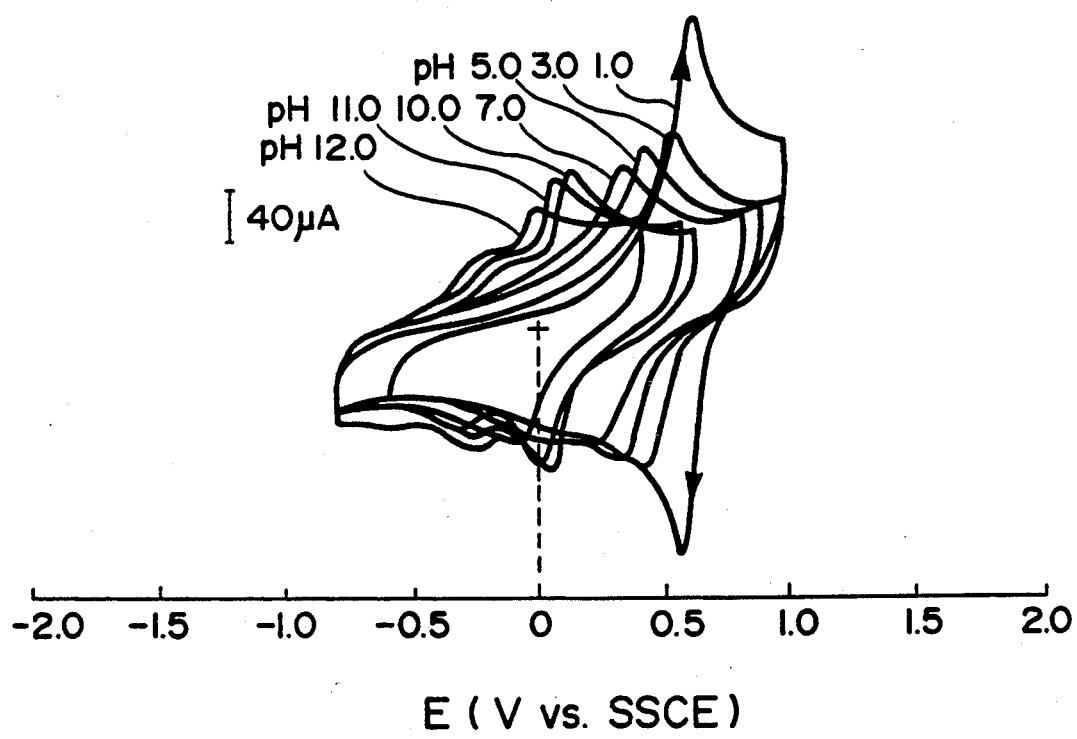
FIG. 6B is a graph showing a potential response of a poly(p,p'-biphenol) membrane.

FIG. 6A shows a cyclic voltamogram of electrolysis.
FIG. 6B shows a response obtained when the poly(p,p'-biphenol) membrane thickness was 10 μm, the pH was changed in a 0.2-M sodium perchlorate solution, and the potential was swept at 200 mV/s.

Then, a lithium ion sensor 4 was dipped on the poly(p,p'-biphenol) polymer membrane 5 under the following conditions. The membrane thickness was 500 μm.

| (Lithium ion-sensitive layer composition) | |
| --- | --- |
| dibenzyl-14-crown-4(6,6-dibenzyl-1,4,8,11-tetraoxacyclo tetradecane) | 1.1 parts by weight |
| o-nitrophenyloctylether | 70.2 parts by weight |
| potassium tetrakis(p-chlorophenyl)borate (K-TCPB) | 0.7 parts by weight |
| polyvinyl chloride (PVC) | 28.0 parts by weight |
| THF solvent | 3 ml |

Then, the other end of the lead wire 3 was connected to the gate portion of the MOSFET 8 to fabricate a lithium ion-sensitive field effect transistor (hereafter referred to as Li-ISFET). This sensor is called a PBP/LSM coated sensor.

COMPARATIVE EXAMPLE

An Li-ISFET was fabricated following the same procedures as in the above example except that the poly(p,p'-biphenol) polymer membrane 5 was not coated but a lithium ion-sensitive layer having the same composition as the above example was directly coated. This sensor is called an LSM coated sensor.

EXPERIMENT 1

A response of each of the Li-ISFETs fabricated in the example and the comparative example was tested in a 150-mM NaCl solution while the concentration of Li was changed from 1.86 to 3.00 mM.

The results are shown in FIG. 2. As shown in FIG. 2, it took 10 seconds to a response of 90% in the example and 2 to 3 seconds in the comparative example. Both values are sufficient as a speed of response.

EXPERIMENT 2

A relationship between the Li$^+$ ion concentration and an output voltage of each of the Li-ISFETs fabricated in the example and the comparative example was tested under the conditions that the NaCl solution was maintained at 150 mM and a pLi was changed from −5.2 to −1.9 in a nitrogen atmosphere at a temperature of 25° C.

The results are shown in FIG. 3. As shown in FIG. 3, the plot has linearity within the pLi range of 1.9 to 2.7. At this time, the slope of the both plots was 52 m/pLi. Since the Li$^+$ ion concentration concerning a patient suffering from manic depressive psychosis is around 10$^{-3}$ M, measurement can be performed within a linear region. Therefore, an accurate measurement result can be expected.

EXPERIMENT 3

Selection coefficients $K_{Li,Na}^{Pot}$ and $K_{Li,K}^{Pot}$ of each the Li-ISFETs fabricated in the example and the comparative example with respect to sodium ions or potassium ions were measured.

The results obtained were, respectively, $K_{Li,Na}^{Pot}=3.3\times 10^{-10}$ and $K_{Li,K}^{Pot}=6.2\times 10^{-3}$. It is assumed that values are smaller with respect to other ions than sodium ions and potassium ions.

EXPERIMENT 4

An influence of dissolved oxygen gas on each of the Li-ISFETs fabricated in the example and the comparative example was tested by alternately supplying O$_2$ gas and N$_2$ gas into a 150-mM NaCl (ph=5.55+0.03) containing 1-mM LiCl.

Figure 4:
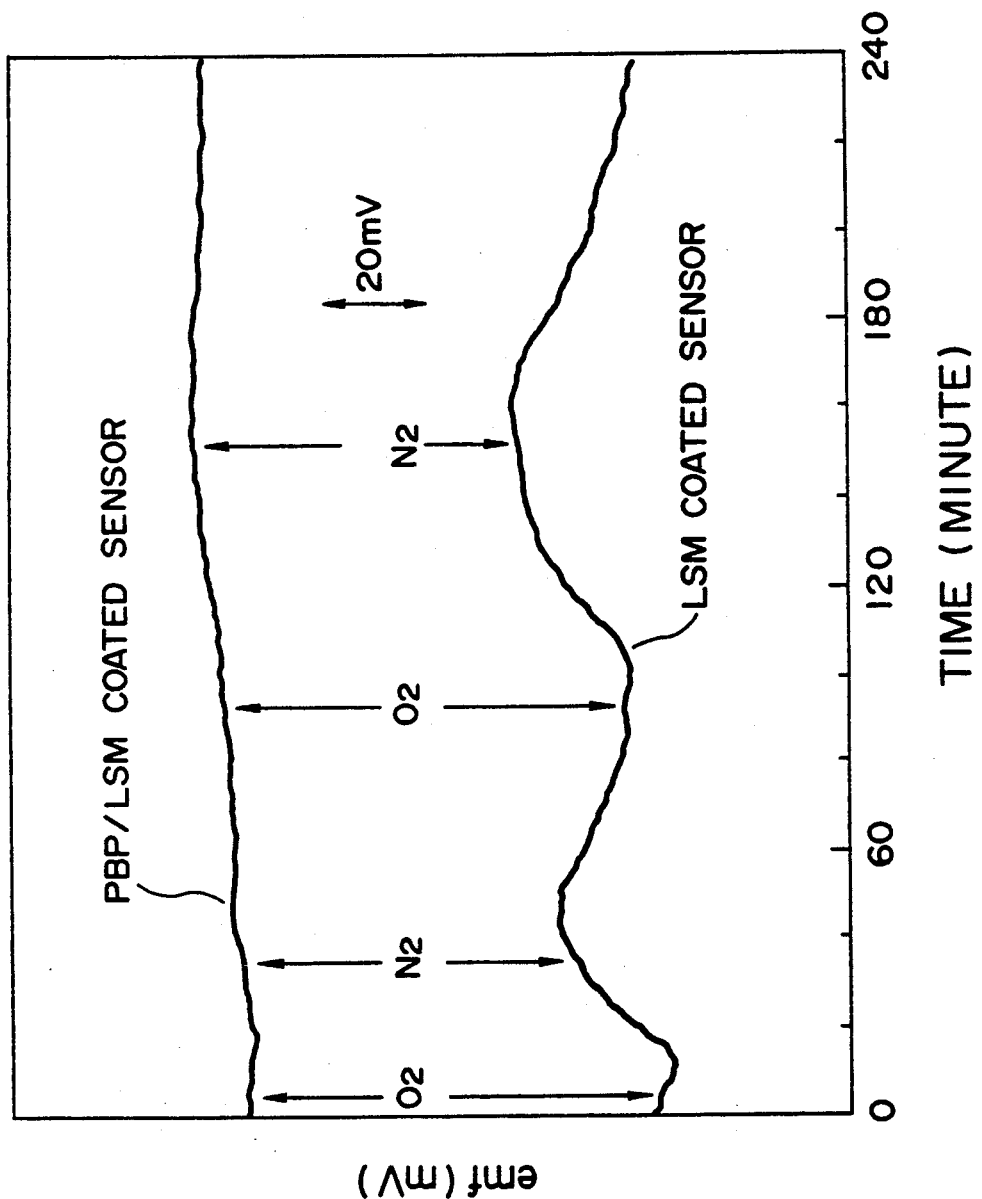
FIG. 4 is a graph showing an influence of oxygen gas to the lithium ion sensor of the embodiment.

The results are shown in FIG. 4. As shown in FIG. 4, the Li-ISFET coated with the poly(p,p'-biphenol) polymer membrane fabricated in the example was less adversely affected by the oxygen gas than that fabricated in the comparative example.

EXPERIMENT 5

The change over time of a slope of each of the Li-ISFETs fabricated in the example and the comparative example obtained when the Li ion concentration was increased in a 150-mM NaCl solution was tested. In this experiment, the electrode portion was preserved in a 150-mM NaCl solution containing 1-mM LiCl.

The results are shown in FIG. 5. As shown in FIG. 5, the Li-ISFET coated with the poly(p,p'-biphenol) polymer membrane had sufficiently stable characteristics in terms of the change over time. Note that the same effect was obtained when a derivative of dibenzyl-14-crown-4 was used in place of dibenzyl-14-crown-4.

As has been described above, the lithium ion sensor according to the present invention can accurately detect and measure a lithium concentration in a body. In addition, the lithium ion sensor is less adversely affected by other ions such as sodium ions or potassium ions.

Since the lithium ion sensor can be made thinner than a hair, it can be inserted in a body without pain.

The lithium ion sensor is not adversely affected by oxygen gas and therefore can be stably used over a month or more.

Since the lithium ion sensor is of a solid type, it can be sterilized with a heated steam and easily handled.

The lithium ion-sensitive layer is a thin organic membrane and is not adversely affected by coagulation of blood in a body. Therefore, a countermeasure against coagulation can be easily taken.

The structure of the lithium sensor fabricated in the above embodiment is merely a preferable example. Therefore, as described above at the beginning of DESCRIPTION OF THE PREFERRED EMBODIMENT in this specification, it is obvious that the same effects as in the above embodiment can be achieved by a lithium ion sensor fabricated by directly coating a gate isolating membrane of a FET, by a lithium ion sensor using other electrically conductive substrates, or in a redox layer and a lithium ion-sensitive layer.

As many apparently widely different embodiments of the present invention can be made without departing from the spirit and scope thereof, it is to be understood that the invention is not limited to the specific embodiments thereof except as defined in the appended claims.

What we claim is:

1. A lithium ion sensor comprising:
   a FET;
   a redox layer having a redox function covering a gate isolating membrane of said FET wherein said redox layer is obtained by electrolytically polymerizing a p-p'biphenol; and
   a lithium ion-sensitive layer for selectively sensing lithium ion covering said redox layer, said lithium ion-sensitive layer being a polyvinyl chloride layer containing dibenzyl-14-crown-4, a derivative of dibenzyl-14-crown-4 or a mixture thereof, dioxaheptyl-dodecyl-14-crown-4, a derivative of dioxaheptyl-dodecyl-14-crown-4 or a mixture thereof, or diethoxyphosphorioxyethyl-dodecyl-14-crown-4, a derivative of diethoxyphosphorioxyethyl-dodecyl-14-crown-4 or a mixture thereof.

2. The lithium ion sensor according to claim 1, wherein said FET is a MOSFET.

3. A lithium ion sensor comprising:
   an electrically conductive substrate having an electrically conductive carbon layer on a surface thereof;
   a redox layer having a redox function covering a surface of said electrically conductive carbon layer wherein said redox layer is obtained by electrolytically polymerizing a p-p'biphenol; and
   a lithium ion-sensitive layer for selectively sensing lithium ion covering said redox layer, said lithium ion-sensitive layer being a polyvinyl chloride layer containing dibenzyl-14-crown-4, a derivative of dibenzyl-14-crown-4 or a mixture thereof, dioxaheptyl-dodecyl-14-crown-4, a derivative of dioxaheptyl-dodecyl-14-crown-4 or a mixture thereof, or diethoxyphosphorioxyethyl-dodecyl-14-crown-4, a derivative of diethoxyphosphorioxyethyl-dodecyl-14-crown-4 or a mixture thereof.

4. A lithium ion sensor comprising:
   a FET;
   a redox layer having a redox function covering a gate isolating member of said FET wherein said redox layer is obtained by electrolytically polymerizing a p-p'biphenol, and
   a lithium ion-sensitive layer for selectively sensing lithium ion covering acid redox layer, said lithium ion-sensitive layer containing 1,1 parts by weight of dibenzyl-14-crown-4, a derivative of dibenzyl-14-crown-4 or a mixture thereof, dioxaheptyldodecyl-14-crown-4, a derivative of dioxaheptyl-dodecyl-14-crown-4 or a mixture thereof, or diethoxyphosphorioxyethyl-dodecyl-14-crown-4, a derivative of diethoxyphosphorioxyethyl-dodecyl-14-crown-4 or a mixture thereof, 70.2 parts by weight o-nitrophenyloctylether, 0.7 parts by weight potassium tetrakis(p-chlorophenyl)borate, 28.0 parts by weight polyvinyl chloride and 3 ml solvent.

5. The lithium ion sensor according to claim 4, wherein said FET is a MOSFET.

6. A lithium ion sensor comprising:
   an electrically conductive substrate having an electrically conductive carbon layer on a surface thereof;
   a redox layer having a redox function covering a surface of said electrically conductive carbon layer wherein said redox layer is obtained by electrolytically polymerizing a p-p'biphenol; and
   a lithium ion-sensitive layer for selectively sensing lithium ion covering said redox layer, said lithium ion-sensitive layer containing 1.1 parts by weight dibenzyl-14-crown-4, a derivative of dibenzyl-14-crown-4 or a mixture thereof, dioxaheptyl-dodecyl-14-crown-4, a derivative of dioxaheptyl-dodecyl-14-crown-4 or a mixture thereof, or diethoxyphosphorioxyethyl-dodecyl-14-crown-4, a derivative of diethoxyphosphorioxyethyl-dodecyl-14-crown-4 or a mixture thereof, 70.2 parts by weight o-nitrophenyloctylether, 0.7 parts by weight potassium tetrakis(p-chlorophenyl)borate, 28.0 parts by weight polyvinyl chloride and 3 ml solvent.

* * * * *

UNITED STATES PATENT AND TRADEMARK OFFICE
CERTIFICATE OF CORRECTION

PATENT NO. : 5,192,417
DATED : March 9, 1993
INVENTOR(S) : Noboru OYAMA et al It is certified that error appears in the above-identified patent and that said Letters Patent is hereby corrected as shown below:

In Column 6, line 35, delete "represents" and -- represent --.

In Column 8, line 38, delete "$K_{LiNo}^{Pot}$" and insert -- $K_{Li.Na}^{Pot}$ --.

In Column 8, lines 43-44, delete "$K_{Li.Nd}^{Pot}$" and insert -- $K_{Li.Na}^{Pot}$ --.

In Column 8, line 51, delete "+" and insert -- ± --.

In Column 10, line 18, delete "member" and insert -- membrane --.

In Column 10, line 22, delete "acid" and insert -- said --.

Signed and Sealed this

Sixteenth Day of November, 1993

*Attest:*

BRUCE LEHMAN

*Attesting Officer*     *Commissioner of Patents and Trademarks*